United States Patent [19]
Yamamoto et al.

[11] Patent Number: 5,584,828
[45] Date of Patent: Dec. 17, 1996

[54] DISPOSABLE DIAPER

[75] Inventors: Masamitsu Yamamoto; Takamitsu Igaue, both of Kawanoe; Yoshihisa Fujioka, Kagawa-ken; Hirotomo Mukai, Kawanoe, all of Japan

[73] Assignee: Uni-Charm Corporation, Ehime-ken, Japan

[21] Appl. No.: 425,564

[22] Filed: Apr. 20, 1995

[30] Foreign Application Priority Data

Apr. 21, 1994 [JP] Japan ..................................... 6-082922

[51] Int. Cl.$^6$ ....................................................... A61F 13/15
[52] U.S. Cl. ............................................................. 604/385.2
[58] Field of Search .............................. 604/358, 385.1, 604/385.2

[56] References Cited

U.S. PATENT DOCUMENTS 4,695,278  9/1987  Lawson .
5,167,653  12/1992  Igaue et al. ........................... 604/385.2

FOREIGN PATENT DOCUMENTS 4-297256  10/1992  Japan ................................. 604/385.2
2212382   7/1989   United Kingdom ................ 604/385.2
9309739   5/1993   WIPO ................................ 604/385.2

*Primary Examiner*—Mary Beth Jones
*Attorney, Agent, or Firm*—Lowe, Price, LeBlanc & Becker

[57] ABSTRACT

A disposable diaper is provided with a pair of elastic cuffs longitudinally extending along transversely opposite sides of a diaper across front and rear sections as well as a crotch section, the cuffs being folded back inwardly of the diaper at intermediate regions of the respective cuffs which extend outwardly from their fixedly bonded side edges, respectively.

2 Claims, 4 Drawing Sheets

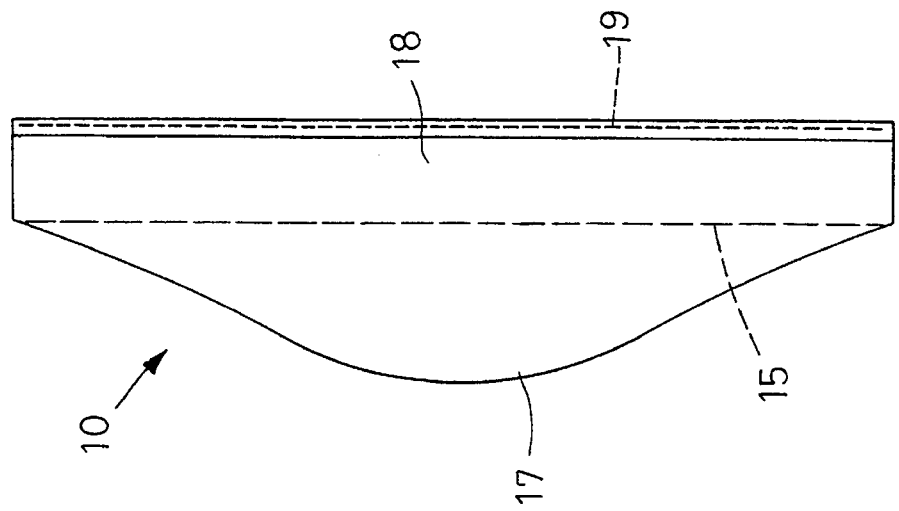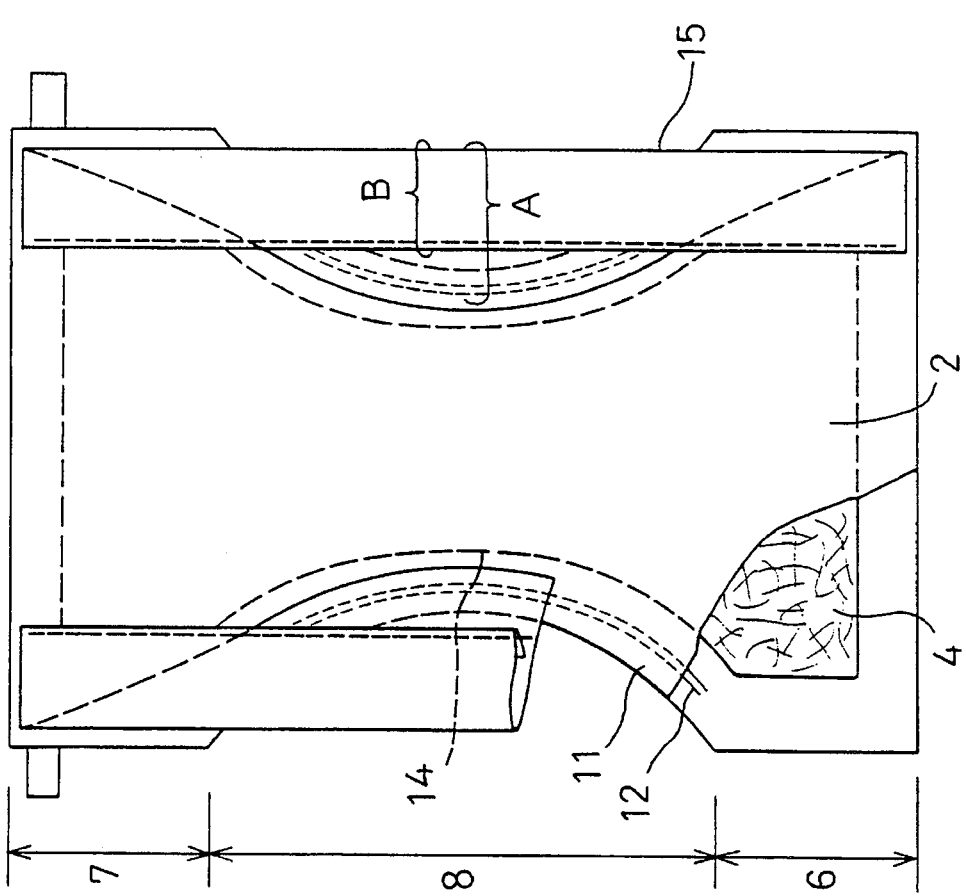

5,584,828

DISPOSABLE DIAPER

BACKGROUND OF THE INVENTION

The present invention relates to a disposable diaper.

Disposable diapers are well known, in which a pair of cuffs longitudinally extend on the inner surface of the diaper along the transversely opposite sides thereof across front and rear sections as well as a crotch section and normally tend to be risen on the inner surface and in order to prevent body fluids from leaking laterally of the diaper.

FIG. 5 in the accompanying drawings is a plan view exemplarily showing such a known disposable diaper as partially broken away. The diaper 1 has a basic body 5 comprising a liquid-permeable topsheet 2, a liquid-impermeable backsheet 3 and an hourglass-shaped liquid-absorbent core 4 sandwiched between these two sheets 2, 3 so as to form a front section 6, a rear section 7 and a crotch section 8 interposed between these two sections 6, 7 longitudinally of the diaper 1. A pair of cuffs 10 longitudinally extend along transversely opposite sides of the basic body 5 across the front and rear sections 6, 7 as well as the crotch section 8 so that these cuffs 10 may bear against the wearer's crotch as the diaper 1 is worn. Additionally, the basic body 5 is provided with elastic members (first elastic members) 11 extending along transversely opposite side edges thereof and bonded in their stretched states to the inner surface of the backsheet 3 for fitness around the respective legs of the user. A pair of tape fasteners 12 outwardly extend from transversely opposite side edges of the rear section 7. Each of the cuffs 10 comprises a rectangular strip of sheet having a width W except its margin for bonding. The cuff 10 has an inner side edge 15 which is a free edge and to which an elastic member (second elastic member) 16 is bonded in its longitudinally stretched state, and an outer side edge 17 extending in parallel to the inner side edge 15. The outer side edge 17 and longitudinally opposite ends 18, 19 of the cuff 10 are bonded to the inner surface of the diaper's basic body 5. With such diaper 1 being worn, the cuff 10 is biased under the contraction of the second elastic member 16 to be risen on the topsheet 2 and to form together with the topsheet 2 a pocket (not shown) opening inwardly of the diaper 1. The cuff 10 forms a barrier which has a height corresponding to the width W and serves against excretion leakage as the cuff 10 is risen substantially in the vertical direction in the crotch zone 8. Such diaper 1 is disclosed, for example, in U.S. Pat. No. 4,695,278.

Slip down of the diaper worn may often cause a gap to be formed between the diaper and the user's crotch, possibly leading to excretion leakage. Certainly, it will be possible to avoid such excretion leakage if the cuffs form sufficiently high barriers when they are risen. To achieve this with the above-mentioned known diaper, the width W may be dimensioned to be correspondingly large. However, the larger the width W is, the larger the extent of the topsheet may be covered by the cuffs and the smaller the area of the topsheet effective for excretion-permeation may be. Thus the lateral leakage of excretion will be rather apt to occur.

In view of the problems as mentioned above, it is a principal object of the invention to provide an improved arrangement of the cuffs, in which each cuff extending outward is folded back inwardly of a diaper along a transversely middle line of the cuff at least in a crotch section of the diaper so that the desired absorbing function of the diaper may be assured even if the width of each cuff is dimensioned to be relatively large.

SUMMARY OF THE INVENTION

The object set forth above is achieved, according to the invention, by a disposable diaper comprising a liquid-permeable topsheet, a liquid-impermeable backsheet, a liquid-absorbent core sandwiched between said top- and backsheets longitudinally forming a front section, a rear section and a crotch section interposed between said front and rear sections, a pair of elasticized leg surrounding side flaps extending outwardly of transversely opposite sides of said core, and a pair of elasticized cuffs longitudinally extending on the inner surface of said side flaps along transversely opposite side edges of said core across said front and rear sections as well as said crotch section and normally tending to be risen on said surface, wherein each of said cuffs has one side edge and longitudinally opposite ends, these ends being fixedly bonded to said inner surface, a free side edge opposed to said fixed bended side edge and an intermediate region extending between said fixedly bonded side edge and said free side edge, and each of said cuffs is inwardly folded back at said intermediate region at least in said crotch section.

With the diaper of the invention, the cuffs do not cover the topsheet over an unacceptably large area even when the width of each cuff is dimensioned to be relatively large, since the cuffs extending outward are folded back inwardly of the diaper at least in the crotch section.

BRIEF DESCRIPTION OF THE DRAWINGS

FIG. 4A shows a modification of a diaper according to the present invention in a partially broken away plan view;

FIG. 4B is a detail view of the cuff of the diaper of FIG. 4A; and

PREFERRED EMBODIMENTS OF THE INVENTION

Figure 1:
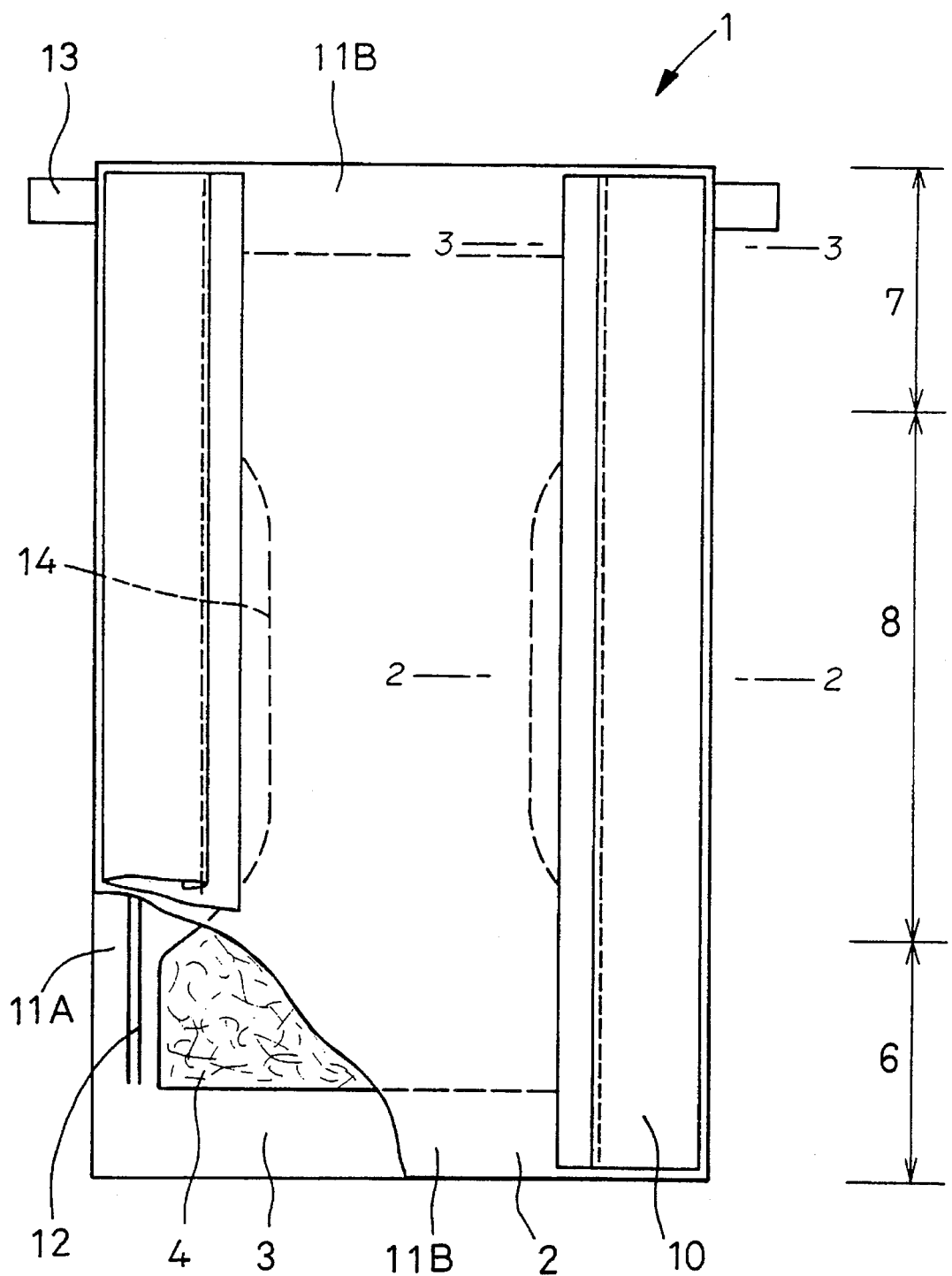
FIG. 1 is a plan view showing an embodiment of a diaper according to the invention as partially broken away.

Referring to FIG. 1, a diaper 1 comprises a liquid-permeable topsheet 2, a liquid-impermeable backsheet 3 and a liquid-absorbent core 4 sandwiched between these two sheets 2, 3, longitudinally forming a front section 6, a rear section 7 and a crotch section 8 interposed between these two sections 6, 7. The liquid-absorbent core 4 is hourglass-shaped and provided along transversely opposite sides thereof with notches 14 contributing to a good fitness of the diaper 1 around the respective legs of the wearer. The top- and backsheets 2, 3 outwardly extend from the periphery of the liquid-absorbent core 4 and are water-tightly bonded together in these outwardly extending regions to form leg surrounding side flaps 11A and waist surrounding flaps 11B of the front and rear sections 6, 7, respectively. A pair of cuffs 10 longitudinally extend on the inner surface of the side flaps 11A along transversely opposite side edges of the core 4 across the front section 6, the crotch section 8 and the rear section 7. Each of the side flaps 11A contains therein an elastic member (first elastic member) 12 sandwiched between the top- and backsheets 2, 3 adjacent the outer side edge of the side flap 11A, and continuously or intermittently bonded to them as it is being stretched longitudinally of the diaper 1. A pair of tape fasteners 13 outwardly extend from transversely opposite side edges of the rear section 7, respectively.

Figure 2:
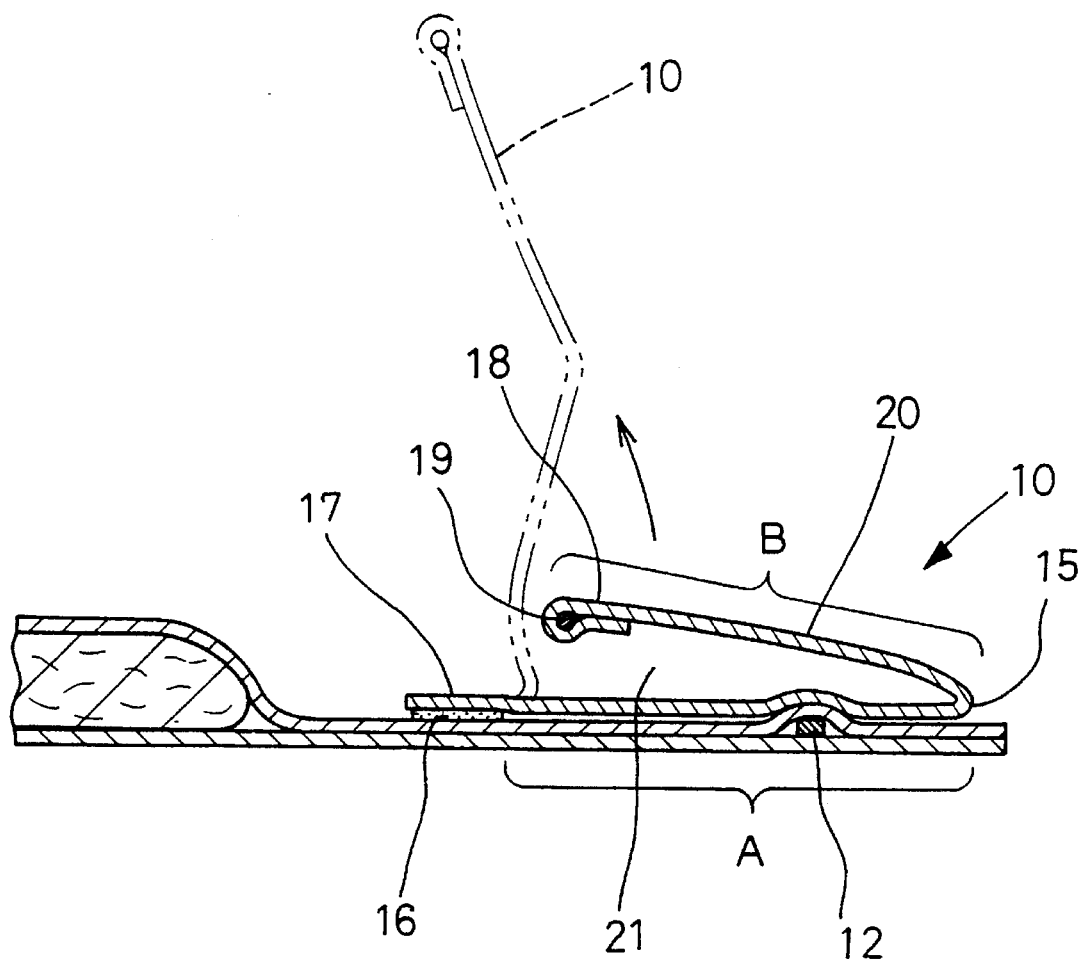
FIG. 2 is a sectional view taken along a line 2—2 in FIG. 1.

Referring to FIG. 2, the cuff 10 comprises a strip of sheet having a soft touch such as a nonwoven fabric, preferably a strip of liquid-impermeable sheet, more preferably a strip of airpermeable but liquid-impermeable sheet and has been inwardly folded along a folding line 15 extending longitudinally of the diaper 1. One side edge of the cuff 10 is bonded by hot melt adhesive 16 to the topsheet 2 to define a fixed edge 17 and the other side edge defines a free edge 18 to which an elastic member (second elastic member) 19 is bonded as it is being stretched longitudinally of the diaper 1. An intermediate region 20 including said folding line 15 is defined between the fixed edge 17 and the free edge 18 and comprises a region corresponding to a width A from the fixed edge 17 to the folding line 15 and a region corresponding to a width B from the folding line 15 to the free edge 18. The region corresponding to the width A is laid above the first elastic member 12. Such cuff 10 forms a pocket 21 opening inwardly of the diaper 1.

Figure 3:
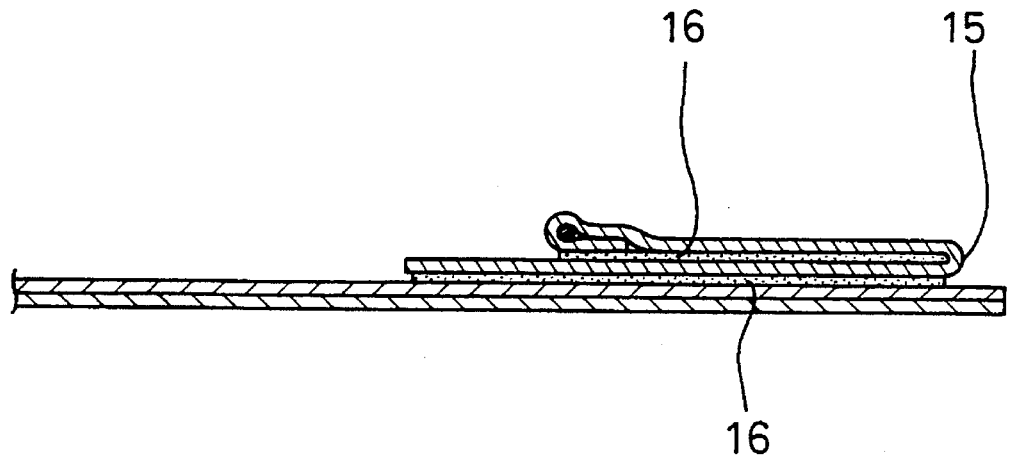
FIG. 3 is a sectional view taken along a line 3—3 in FIG. 1.
Figure 5:
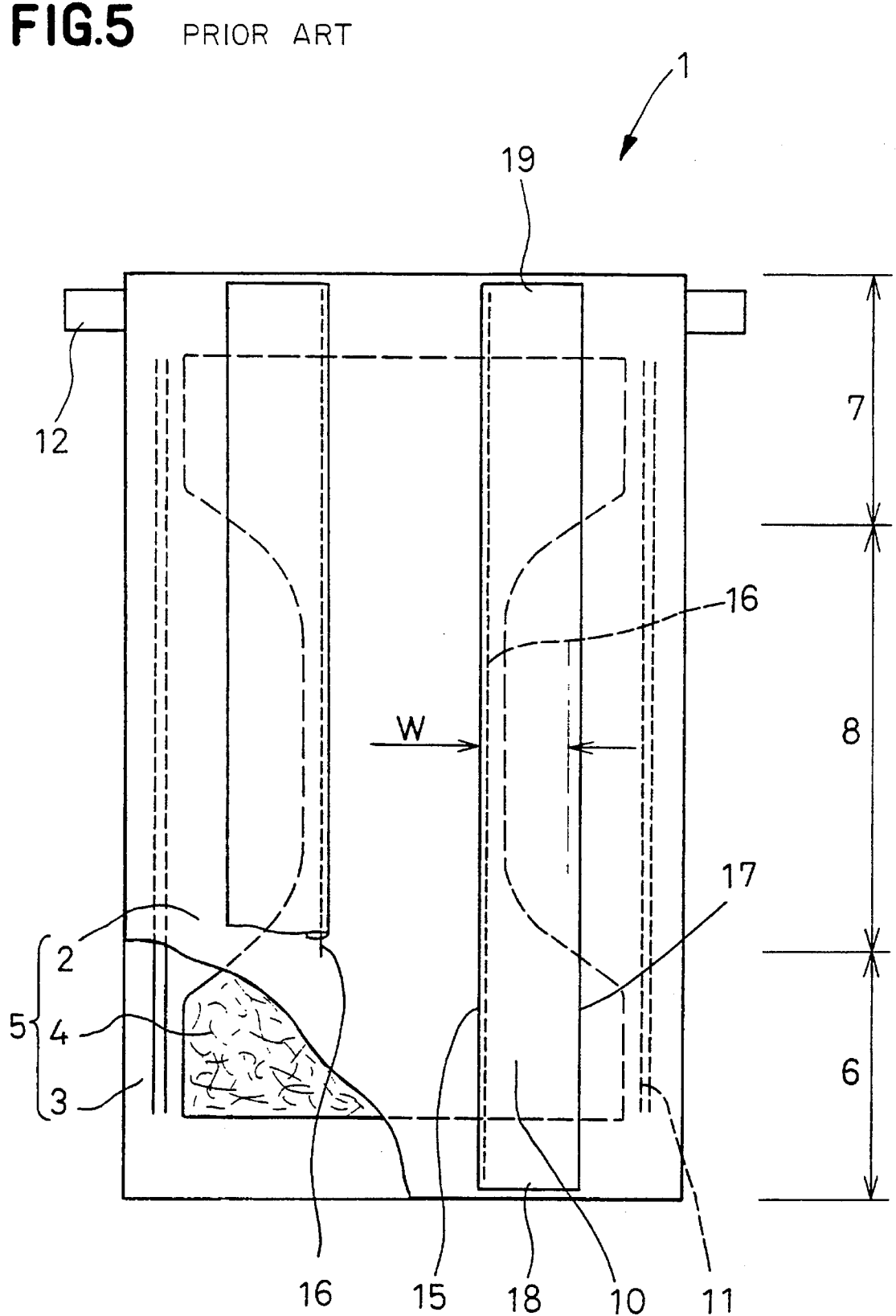
FIG. 5 is a plan view showing a well known diaper.

Referring to FIG. 3, longitudinally rear ends of the cuff 10 has one surface put one on another by folding it back onto itself and bonded by hot melt adhesive 16 together and the other surface opposed to the topsheet 2 bonded also by hot melt adhesive 16 to the topsheet 2. Consequently, the pocket is in its closed state as far as this region is concerned. It should be understood that the longitudinally front end of the cuff 10 is constructed in the same manner as the longitudinally rear end is constructed.

With the diaper 1 of such construction being worn, the diaper 1 is curved inwardly along the longitudinal direction thereof and simultaneously the second elastic member 19 contracts. As indicated by imaginary lines in FIG. 2, the contraction of the second elastic member 19 rises the cuff 10 inside the diaper 1 and thereby forms a barrier having a height corresponding substantially to the total width A plus B of the cuff 10 in the crotch section 8. The free edge 18 of the cuff 10 is bonded with its longitudinally front and rear ends to the inner surface of the diaper 1 and therefore the barrier has its height progressively reduced toward these ends.

Referring to FIGS. 4(A) and 4(B) in a variant of the diaper 1, portions of front and rear sections 6, 7 extending outwardly from respective notches 14 of an hourglass-shaped liquid-absorbent core 4 are bonded together and cut out in parallel to the respective notches 14, i.e., in circular-arc-shape to form leg surrounding flaps 11. Each of these flaps 11 contains therein first elastic member 12 extending in parallel to the notch 14 and bonded to the top- and backsheets 2, 3 as it is being stretched longitudinally of a diaper. As shown by the detail view of FIG. 4(B), a cuff 10 has a fixed edge 17 bordered by a curved line describing a circular arc substantially in parallel to the flap 11 and a free edge 18 bordered by a straight line extending longitudinally of the diaper, immediately inside and in parallel to which a second elastic member 19 bonded in its stretched state to the cuff 10. The extend defined between these two edges 17, 18 is adapted to be folded back along a broken line 15 onto itself. The cuff 10 is attached to the basic body of the diaper with the fixed edge 17 being bonded to the inner surface of the associated flap 11 and the free edge 18 being inwardly folded back along the broken line 15 toward the inner surface of the diaper followed by bonding at the longitudinally opposite ends lying outside the corresponding ends of the liquid-absorbent core 4 to the inner surface of the diaper. In this manner, the cuff 10 can form in a crotch section 8 the barrier of which the height corresponds substantially to the total width A plus B of this cuff 10 without an apprehension that the effective area of the topsheet 2 for liquid-permeation might be unacceptably reduced due to bonding the cuff 10 to the topsheet 2, since the cuff 10 is substantially not bonded to the region of the topsheet 2 covering the liquid-absorbent core 4. Furthermore, these is no apprehension that the cuff 10 may make the diaper 1 bulky along the waist line and thereby make the diaper uncomfortable to wear, since the cuff 10 is folded back onto itself only in the crotch section 8 but substantially not at the longitudinally opposite ends of the diaper.

It is also possible without departure from the scope of the invention to form the cuff 10 as a whole by an elastic sheet such as elastomeric sheet. In this case, such sheet may be bonded in its stretched state to the inner surface of the diaper without demand for use of the second elastic member 19. The top- and backsheets 2, 3 as well as the liquid-absorbent core 4 may be made of materials usually employed in this technical field. For bonding of the respective members, adhesive such as hot melt type adhesive or glue, or welding technique may be employed. If desired, elastic members may be bonded to the diaper also along the waist line to make the waist line elastic.

With the disposable diaper of the invention, there is no apprehension that the cuff may cover the topsheet over its unacceptably large area, reducing the effective area of the topsheet for liquid permeation capacity, even if the cuff is dimensioned to be relatively wide.

Such cuff forms the pocket opening inwardly of the diaper when the cuff is not risen to prevent excretion from laterally leaking and forms the high barrier when the cuff is risen to stop up a gap possibly formed between the diaper and the wearer's crotch and thereby also to prevent possibly resulting lateral leakage of excretion.

What is claimed is:

1. A disposable diaper comprising:

a liquid-permeable topsheet;

a liquid-impermeable backsheet;

a liquid-absorbent core sandwiched between said topsheet and said backsheet longitudinally forming a front section, a rear section and a crotch section interposed between said front and rear sections;

a pair of elasticized leg surrounding side flaps extending outwardly of transversely opposite sides of said core and including an inner surface, said side flaps being elasticized with a first elastic member disposed longitudinally adjacent an outer side edge of said side flap; and a pair of elasticized cuffs longitudinally extending on said inner surface of said side flaps along transversely opposite side edges of said core across said front section, said rear section and said crotch section and normally tending to be risen on said surface;

wherein each of said cuffs includes a fixed bonded side edge, longitudinally opposite ends, a free side edge opposed to said fixed bonded side edge, and an intermediate region extending between said fixedly bonded side edge and said free side edge, the longitudinally opposite ends being fixedly bonded to said inner surface;

wherein said fixed bonded side edge is fixedly bonded to said inner surface outwardly of said core at said crotch section;

wherein each of said cuffs is inwardly folded back at said intermediate region at least in said crotch section to form a fold line;

wherein each of said cuffs is elasticized with a second elastic member disposed longitudinally adjacent said free edge of said cuff, and said intermediate region of said cuff is laid above said first elastic member; and wherein the fixed edge of said cuff is spaced inwardly a first distance from the outer edge of said side flap, wherein said fold line is substantially located between said outer edge of said side flap and said first elastic member, and wherein a second distance between said free side edge and said fold line is less than said first distance to form a barrier with a height corresponding substantially to the total of the first and second distances.

2. A disposable diaper according to claim 1, wherein said fold line is substantially located at said outer edge of said side flap.

* * * * *